United States Patent
Mironov et al.

(10) Patent No.: US 10,017,430 B2
(45) Date of Patent: *Jul. 10, 2018

(54) ALKANE-ALKENE COUPLING VIA TANDEM ALKANE-DEHYDROGENATION/ALKENE-DIMERIZATION CATALYZED BY PINCER IRIDIUM CATALYST HETEROGENIZED ON SOLID SUPPORTS

(71) Applicants: Chevron U.S.A. Inc., San Ramon, CA (US); Rutgers, The State University of New Jersey, New Brunswick, NJ (US)

(72) Inventors: Oleg Mironov, San Ramon, CA (US); Robert J. Saxton, San Ramon, CA (US); Alan S. Goldman, Highland, NJ (US); Akshai Kumar, New Brunswick, NJ (US)

(73) Assignees: Chevron U.S.A. Inc., San Ramon, CA (US); Rutgers, The State University of New Jersey, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/664,333

(22) Filed: Jul. 31, 2017

(65) Prior Publication Data
US 2018/0044261 A1    Feb. 15, 2018

Related U.S. Application Data

(60) Provisional application No. 62/374,662, filed on Aug. 12, 2016.

(51) Int. Cl.
  *C07C 2/36*    (2006.01)
  *C07C 5/42*    (2006.01)
  *B01J 31/24*   (2006.01)

(52) U.S. Cl.
  CPC ............... *C07C 2/36* (2013.01); *B01J 31/24* (2013.01); *B01J 2231/20* (2013.01); *B01J 2531/827* (2013.01); *C07C 2521/14* (2013.01); *C07C 2531/24* (2013.01)

(58) Field of Classification Search
None
See application file for complete search history.

(56) References Cited

U.S. PATENT DOCUMENTS

| | | |
|---|---|---|
| 2,620,347 A | 12/1952 | Rottig |
| 4,805,561 A | 2/1989 | Davis et al. |
| 4,959,080 A | 9/1990 | Sternling |
| 5,620,676 A | 4/1997 | Jacobson et al. |
| 5,780,701 A | 7/1998 | Kaska et al. |
| 5,811,363 A | 9/1998 | Leviness et al. |
| 5,817,701 A | 10/1998 | Leviness et al. |
| 5,821,270 A | 10/1998 | Chang et al. |
| 6,068,760 A | 5/2000 | Benham et al. |
| 6,201,030 B1 | 3/2001 | Beer |
| 6,217,830 B1 | 4/2001 | Roberts et al. |
| 6,838,487 B1 | 1/2005 | Demirel et al. |
| 6,880,635 B2 | 4/2005 | Vinegar et al. |
| 6,982,305 B2 | 1/2006 | Nagy |
| 9,278,894 B2 | 3/2016 | Goldman et al. |
| 9,802,971 B2* | 10/2017 | Kumar ............. C07C 5/52 |
| 2010/0236984 A1* | 9/2010 | Brookhart ......... B01J 23/36 208/121 |
| 2013/0123552 A1 | 5/2013 | Goldman |
| 2015/0251171 A1* | 9/2015 | Kumar ............. C07C 5/52 585/656 |
| 2018/0002361 A1* | 1/2018 | Kumar ............. C07F 15/0033 |

OTHER PUBLICATIONS

Gupta, M., et al., "A highly active alkane dehydrogenation catalyst: stabilization of dihydrido rhodium and iridium complexes by a P—C—P pincer ligand", Chem. Commun., (1996) 2083-2084.
Liu, Fuchen and Alan S. Goldman, "Efficient thermochemical alkane dehydrogenation and isomerization catalyzed by an iridium pincer complex," Chem. Comm. 1999, 655-656.
Crabtree, R. H., et al., "Iridium Complexes in Alkane Dehydrogenation", J. Am. Chem. Soc., 101(26):7738-7740 (1979).
Kumar, A., et al., "Dehydrogentation of n-Alkanes by Solid-Phase Molecular Pincer-Iridium Catalysts. High Yields of α-Olefin Product", J. Am. Chem. Soc., 137:9894-9911 (2015).
Huang, Z., et al., "Highly Active and Recyclable Heterogeneous Iridium Pincer Catalysts for Transfer Dehydrogenation of Alkanes", Adv. Synth. Catal., 2009, 351(1-2):188-206.
Huang, Z., et al., "Efficient Heterogeneous Dual Catalyst Systems for Alkane Metathesis", Adv. Synth. Catal., 352: 125-135 (2010).
Adams, J. J., et al, "Acceptor pincer Ru(II) chemistry", Dalton Trans., 2012, 41:12601-12611.
Adams, J. J., et al , "Investigation of Iridium CF3 PCP Pincer Catalytic Dehydrogenation and Decarbonylation Chemistry", Organometallics, 2012, 31:1439-1447.
Adams, J. J., et al., "Acceptor PCP Pincer Iridium Chemistry: (CF3PCP)IrIII Coordination Properties", Organometallics, 2011, 30:689-696.
Yao, W., et al., "Selective Catalytic Transfer Dehydrogenation of Alkanes and Heterocycles by an Iridium Pincer Complex", Angew. Chem., Intl. Ed., 2014, 53:1390-1394.
Roddick, D. M., Tuning of PCP Pincer Ligand Electronic and Steric Properties, Top. Organomet. Chem., 2013, 40:49-88.
Allen, K E., et al., "Alkane Dehydrogenation by C—H Activation at Iridium(III)", Organometallics, 2013, 32:1579-1582.
Allen, K E., et al., "Regeneration of an Iridium(III) Complex Active for Alkane Dehydrogenation Using Molecular Oxygen", Organometallics, 2014, 33:1337-1340.

(Continued)

*Primary Examiner* — Philip Y Louie
(74) *Attorney, Agent, or Firm* — Melissa M. Hayworth; E. Joseph Gess; Susan M. Abernathy

(57) ABSTRACT

Disclosed herein are processes for tandem alkene dehydrogenation/alkene dimerization using an iridium pincer complex catalyst on a support comprising magnesium silicates (e.g., Florisil®). The reaction process comprises providing an iridium pincer complex bound to a solid support comprising magnesium silicates; providing a gaseous alkane feedstock comprising at least one alkane; and contacting the gaseous alkane feedstock with the iridium pincer complex bound to the solid support in the presence of a hydrogen acceptor to form dimerized alkenes. The processes disclosed herein can accomplish facile, low-temperature tandem transfer dehydrogenation of alkanes and dimerization of alkenes with unprecedented TONs at a reasonable rate of conversion.

20 Claims, No Drawings

(56) References Cited

OTHER PUBLICATIONS

Bezier, D. and Maurice Brookhart, "Applications of PC(sp3)P Iridium Complexes in Transfer Dehydrogenation of Alkanes" ACS Catal., 2014, 4:3411-3420.
Brayton, D. F., et al., "Synthesis, Characterization, and Dehydrogenation Activity of an Iridium Arsenic Based Pincer Catalyst", Organometallics 2014, Ahead of Print.
Chianese, A. R., et al., "Acceptorless Alkane DehydrogenationCatalyzed by Iridium CCC-Pincer Complexes", Organometallics, 2014, 33:457-464.
Chianese, A. R., et al, "Iridium Complexes of Bulky CCC-Pincer N-Heterocyclic Carbene Ligands: Steric Control of Coordination Number and Catalytic Alkene Isomerization", Organometallics, 2012, 31:7359-7367.
Chianese, A. R., et al., "Iridium Complexes of CCC-Pincer N-Heterocyclic Carbene Ligands: Synthesis and Catalytic C—H Functionalization", 2010, Organometallics 29:3019-3026.
Gruver, B. C., et al., "Acceptor Pincer Chemistry of Ruthenium: Catalytic Alkane Dehydrogentation by (CF3PCP)Ru(cod)(H)", Organometallics, 2011, 30:5133-5140.
Gruver, B. C., et al., "Acceptor Pincer Chemistry of Osmium: Catalytic Alkane Dehydrogenation by (CF3PCP)Os(cod)(H)", Organometallics, 2013, 32:6468-6475.
Haenel, M. W., et al., "Thermally Stable Homogeneous Catalysts for Alkane Dehydrogenation", Angew. Chem., Intl. Ed., 2001, 40(19):3596-3600.
Kundu, S., et al., "Rational Design and Synthesis of Highly Active Pincer-Iridium Catalysts for Alkane Dehydrogenation", Organometallics, 2009, 28:5432-5444.
<napp, S. M. M., et al., "Mechanistic Studies of Alkene Isomerization Catalyzed by CCC-Pincer Complexes of Iridium" Organometallics, 2014, 33:473-484.
Leitch, D. C., et al., "Scope and Mechanism of Homogeneous Tantalum-Iridium Tandem Catalytic Alkane/Alkene Upgrading using Sacrificial Hydrogen", Organometallics, 2014, 33:3353-3365.
Punji, B., et al., "A Highly Stable Adamantyl-Substituted Pincer-Ligated Iridium Catalyst for Alkane Dehydrogentation", Organometallics, 2010, 29:2702-2709.
Jia, X., et al., "Iridium complexes of new NCP pincer ligands: catalytic alkane dehydrogenation and alkene isomerization", Chem. Commun. (Cambridge, U. K.), 2014, 50:11056-11059.
Kundu, S., et al., "Synthesis of Piperylene and Toluene via Transfer Dehydrogenation of Pentane and Pentene", ACS Catalysis, 2013, 3:1768-1773.
Lyons, T. W., et al., "Synthesis of p-Xylene from Ethylene", J. Am. Chem. Soc., 2012, 134:15708-15711.
Liu, F. et al., "Dehydrogenation of n-Alkanes Catalyzed by Iridium "Pincer" Complexes: Regioselective Formation of α-Olefins", J. Am. Chem. Soc., 1999, 121:4086-4087.
Haibach, M.C., et al., "Alkane metathesis by tandem alkane-dehydrogenation-olefin-metathesis catalysis and related chemistry", Accounts of Chemical Research, 2012, 45(6):947-958.
Belli, J. and Craig M. Jensen, "Catalytic Alkane Dehydrogenation by IrClH2 (PPri3)2: Evidence for an Alkane Associative Mechanism", Organometallics, 1996,15(6):1532-1534.
Göttker-Schnetmann, I., et al., "Synthesis and Properties of Iridium Bis(phosphinite) Pincer Complexes (p-XPCP)IrH2, (p-XPCP)Ir(CO), (p-XPCP)Ir(H)(aryl), and {(p-XPCP)Ir}2{μ-N2} and Their Relevance in Alkane Transfer Dehydrogenation", Organometallics 2004, 23(8):1766-1776.
Leitch, D.C., et al., "Upgrading Light Hydrocarbons via Tandem Catalysis: A Dual Homogeneous Ta/Ir System for Alkane/Alkene Coupling", J. Am. Chem. Soc., 2013,135(28):10302-10305.
Ahuja, R., et al., "Catalytic dehydroaromalization of n-alkanes by pincer-ligated iridium complexes", Nature Chemistry, 2010, 3(2):167-171.
Goldman, A.S. et al., "Catalytic Alkane Metathesis by Tandem Alkane Dehydrogenation-Olefin Metathesis", Science, 2006, 312(5771):257-261.
Göttker-Schnetmann, I. and Maurice Brookhart, "Mechanistic studies of the transfer dehydrogenation of cyclooctane catalyzed by iridium bis(phosphinite) p-XPCP pincer complexes", J. Am. Chem. Soc., 2004,126(30):9330-9338.
Krogh-Jespersen, K., et al., "On the Mechanism of (PCP)Ir-Catalyzed Acceptorless Dehydrogenation of Alkanes: A Combined Computational and Experimental Study", J. Am. Chem. Soc., 2002,124(38):11404-11416.
Göttker-Schnetmann, I., et al., "Iridium Bis(phosphinite)p-XPCP Pincer Complexes: Highly Active Catalysts for the Transfer Dehydrogenation of Alkanes", J. Am. Chem. Soc., 2004,126(6):1804-1811.
Dobereiner, G. E., et al., "Catalytic Synthesis ofn-Alkyl Arenes through Alkyl Group Cross-Metathesis", J. Am. Chem. Soc., 2013,135(34):12572-12575.
Zhu K., et al., "Highly effective pincer-ligated iridium catalysts for alkane dehydrogenation. DFT calculations of relevant thermodynamic, kinetic, and spectroscopic properties", J. Am. Chem. Soc., 2004,126(40):13044-13053.
Choi, J., et al., "Dehydrogenation and related reactions catalyzed by iridium pincer complexes", Chemical Rev., 2011, 111(3):1761-1779.
Renkema, K.B., et al., "Mechanism of alkane transfer-dehydrogenation catalyzed by a pincer-ligated iridium complex", J. Am. Chem. Soc., 2003,125(26):7770-7771.
Shi, Y., et al., "Highly Active Catalysts for the Transfer Dehydrogenation of Alkanes: Synthesis and Application of Novel 7-6-7 Ring-Based Pincer Iridium Complexes". Chem. Eur. J., 2013, 19(32):10672-10689.
Gupta, M., et al., "Catalytic Dehydrogenation of Cycloalkanes to Arenes by a Dihydrido Iridium P—C—P Pincer Complex", J. Am. Chem. Soc., 1997,119(4):840-841.
Fan, Hua-Jun and Michael B. Hall, "Density functional studies of catalytic alkane dehydrogenation by an iridium pincer complex with and without a hydrogen acceptor", Journal of Molecular Catalysis A: Chemical, 2002, 189(1):111-118.
Burk, M. J. and Robert H. Crabtree, "Selective Catalytic Dehydrogenation of Alkanes to Alkenes" J. Am. Chem. Soc., 1987,109 8025.
Zhang, X., et al., "Novel synthesis of enamines by iridium-catalyzed dehydrogenation of tertiary amines" Chem. Commun. 2003, 2060-2061.
Crabtree, R.H., et al., "Alkane dehydrogenation by iridium complexes", J. Am. Chem. Soc., 1982,104(1):107-113.
Sabuj Kundu et al., "Synthesis of piperylene and toluene via transfer dehydrogenation of pentane and pentene", ACS Catal., 2013, vol. 3, pp. 1768-1773.
Zheng Huang et al., "Efficient heterogeneous dual catalyst systems for alkane metathesis", Adv. Synth. Catal., 2010, vol. 352, pp. 125-135.
Sabuj Kundu et al., "Rational design and synthesis of highly active pincer-iriduim catalyst for alkane dehydrogenation", Organometallics, 2009, vol. 28, pp. 5432-5444.
Gupta, M., et al., "Catalytic dehydrogenation of ethylbenzene and tetrhydrofunan by a dihydrido iridium P—C—P pincer complex", Chem. Commun. 1997, 461-462.
Jensen, C. M., "Iridium PCP pincer complexes: highly active and robust catalysts for novel homogenous aliphatic dehydrogenations" Chem. Comm. 1999, 2443-2449.
Burk, M. J. et al., Thermal and Photochemical Catalytic Dehydrogenation of Alkanes with [IrH2(CF3CO2)(PR3)2] (R=C6H4F-p and Cycolhexyl) J. Chem. Soc., Chem. Commun. 1985, 1829-1830.
Singleton, John T., "The uses of pincer complexes in organic synthesis" Tetrahedron 59 2003, 1837-1857.
Ahuja, R., et al., "Catalytic ring expansion, contraction, and metathesis-polymerization of cycloalkanes", Chem. Commun. 2008, 253-255.
Xu, W., et al., "Thermochemical alkane dehydrogenation catalyzed in solution without the use of a hydrogen acceptor" Chem. Commun. 23 (1997): 2273-2274.
Albrecht, M., and Gerard van Koten, "Platinum Group Organometallics Based on "Pincer" complexes: Sensors, Switches, and Catalysts", Angew. Chem. Int. Ed. 40 2001, Wiley-VCH Verlag GmbH, Weinheim, p. 3751.

(56) References Cited

OTHER PUBLICATIONS

NIST ("Hexane", NIST Chemistry WebBook, SRD 69, http://webbok.nist.gov/cgi/cbook.cgi?ID=C110543&Units=SI&Mask=4&Type=ANTOINE&Plot=on#) Antoine parameters from 1945 & 1973.

* cited by examiner

ALKANE-ALKENE COUPLING VIA TANDEM ALKANE-DEHYDROGENATION/ALKENE-DIMERIZATION CATALYZED BY PINCER IRIDIUM CATALYST HETEROGENIZED ON SOLID SUPPORTS

The present application claims priority to U.S. Provisional No. 62/374,662 filed Aug. 12, 2016 entitled "Alkane-Alkene Coupling Via Tandem Alkane-Dehydrogenation/Alkene-Dimerization Catalyzed by Pincer Iridium Catalyst Heterogenized on Solid Support", the contents of which are incorporated herein by reference in their entirety.

FIELD OF ART

Provided is a method of upgrading low molecular weight hydrocarbons to heavier molecular weight hydrocarbons. More specifically, the process uses iridium princer complex catalysts on solid supports in a tandem dehydrogenation/alkene-dimerization reaction.

BACKGROUND

The rapidly diminishing conventional oil reserves and the ever-increasing demand for liquid fuel (diesel and jet fuel in particular) have stimulated a surge in the global pursuit for non-conventional liquid fuels in the desired $C_7$-$C_{19}$ range. Currently, Fischer-Tropsch catalysis based on syngas oligomerization is a major contributor to non-conventional liquid fuels which can lead to an increase in the production of light alkanes. Light alkanes, $C_1$-$C_5$, are also highly abundant in current world oil and gas reserves. High accumulation of undesirable light alkanes calls for the formulation of efficient methods to upgrade low molecular weight hydrocarbons to heavier molecular weight hydrocarbons in the desirable range of $C_7$-$C_{19}$. One way to transform these abundant alkanes to versatile olefins is via cracking in refining industries. Catalytic cracking processes are often performed at very high temperatures (>500° C.) and thus are limited by reduced energy efficiency and poor product selectivity. In recent years much research has focused on transforming unproductive alkanes to highly versatile olefins with better selectivity and at lower operating temperatures. Transformation through alkanes dehydrogenation has shown some success.

Several homogeneous catalytic systems have been shown to accomplish alkane dehydrogenation at lower temperatures (<250° C.). Recent years have seen progress in dehydrogenation of alkanes and alkyl groups under homogeneous conditions using organometallic systems. A significant milestone in this regard has been the design and use of pincer-ligated iridium complexes for alkane dehydrogenation. The first report of alkane dehydrogenation came from Kaska and Jensen using ($^{tBu4}$PCP)IrH$_n$ (1-H$_n$; $^{R4}$PCP=κ$^3$-C$_6$H$_3$-2,6-(CH$_2$PR$_2$)$_2$; n=2 or 4). (See Gupta, M., et al., Chem. Commun. 1996, 2083). The Goldman group subsequently reported the greater catalytic activity of the less crowded $^{iPr4}$PCP analogue. (See Liu, F., et al., Chem. Commun. 1999, 655). This has been followed by reports of numerous catalytically active variants with the (PCP)Ir motif, including other bis-phosphines, bis-phosphinites (PO-COP), hybrid phosphine-phosphinites (PCOP), arsines (AsOCOAs), hybrid phosphine-thiophosphinites (PSCOP), and hybrid amine-phosphinites (NCOP). These complexes have also been employed for numerous other catalytic transformations of hydrocarbons, including alkane metathesis, alkyl group metathesis, dehydroaromatization, alkane-alkene coupling reactions, borylation of alkanes, and the dehydrogenation of several non-alkane substrates. More recently, several other pincer motifs have been explored for alkane dehydrogenation, such as (PBP)Ir, (CCC)Ir, (PCP)Ru, (PCP)Os, and (NCN)Ir.

Starting with Crabtree's report (Crabtree, R. H.; Mihelcic, J. M.; Quirk, J. M. J. Am. Chem. Soc. 1979, 101, 7738), 3,3-dimethyl-1-butene (TBE) has been used as an effective hydrogen acceptor for alkane transfer dehydrogenation. This is mainly due to the fact that TBE is not only resistant to double-bond isomerization, but also weakly coordinating, thus minimizing inhibition of catalysis. Norbornene (NBE) is also effective, presumably for similar reasons. Crabtree and co-workers had noted that the less bulky ethylene deactivated the catalysts via formation of stable complexes. However on a large scale, the use of smaller olefins, particularly ethylene and propene, would be much more practical. Recent years have seen a surge in the number of reports that describe the use of propene and ethylene as an acceptor for a variety of reactions such as dehydrogenation, dehydroaromatization, synthesis of piperylene, toluene, and p-xylene.

Of particular interest is the dehydrogenation of light alkanes, such as butane and pentane. The resulting primary (olefin) and secondary (dienes) dehydrogenation products are versatile and could potentially be dimerized (or cross-dimerized) to give alkanes of molecular weight more suitable for fuel, for example, in the $C_7$-$C_{19}$ range.

Remarkably high turnover rates in the molecular pincer-iridium catalyzed gas-solid phase transfer-dehydrogenation of light alkanes (which are generally undesirable as transportation fuel components) using economical gaseous olefins such as propene and ethylene have been recently reported. (Kumar, A., et al., J. Am. Chem. Soc. 2015, 137, 9894). The resulting light olefins and dienes have potential applications as precursors for fuel chemicals. In contrast to non-molecular solid-phase systems, these molecular solid-phase systems retained their characteristic behavior in solution and are selective for the formation of α-olefins resulting in yields of α-olefin much greater than have been previously obtained from homogeneous solution phase systems. The gas-solid phase transfer-dehydrogenation can be considered as unsupported heterogeneous reaction as it occurs by coating the molecular pincer-iridium catalyst on the walls of glass. This is thus different from earlier reports where the pincer catalyst is supported on solid supports via polar anchoring groups. (Huang, Z., et al., Adv. Synth. Catal. 2009, 351, 188 and Huang, Z., et al., Adv. Synth. Catal. 2010, 352, 125).

The industry is always searching for improved processes for producing valuable hydrocarbons in the liquid fuels range of $C_7$-$C_{19}$. Effective and efficient processes of transforming light alkanes of minimal value to valuable fuels hydrocarbons in the $C_7$-$C_{19}$ range are of particular interest. One object of the present invention is to provide such a process.

SUMMARY

Disclosed herein is a process for preparing dimerized alkenes in a tandem dehydrogenation/alkene dimerization reaction. The process involves a gas-solid phase transfer-dehydrogenation of light alkanes and also dimerization of the produced alkenes, both catalyzed by pincer-iridium complexes bound to a solid support via a covalent bond. This process produces high value dimerized alkenes.

In one embodiment, a process for producing dimerized alkenes is provided comprising providing an iridium pincer complex bound to a solid support comprising magnesium silicates; providing a gaseous alkane feedstock comprising at least one alkane; and contacting the gaseous alkane feedstock with the iridium pincer complex bound to the solid support in the presence of a hydrogen acceptor to form dimerized alkenes. In one embodiment the support is magnesium silicates (for example, $MgO \cdot \chi SiO_2$ such as Florisil®) and the dimerized alkene products in the $C_7+$ range are recovered. In one embodiment the process further comprises recovering the dimerized alkenes.

In one embodiment, the most efficient catalytic system is obtained by heterogenizing (p-OK-$^{iPr4}$PCP)Ir($C_2H_4$) on magnesium silicates (e.g., Florisil®). The resulting catalytic system not only shows unprecedented rates but also is highly recyclable.

The processes disclosed herein can accomplish facile, low-temperature (less than 300° C.) transfer dehydrogenation of alkanes (e.g., highly abundant alkanes like pentane) with unprecedented selectivities and TONs at a reasonable rate of conversion. In certain embodiments, the processes use readily recyclable and inexpensive hydrogen acceptors. The processes disclosed herein utilize an iridium pincer complex as a catalyst on a solid support of magnesium silicates, which catalyst also exhibits good recyclability. The process can not only provide olefins, but also dimerized olefin products in the desirable $C_7$-$C_{19}$ range.

DETAILED DESCRIPTION

Provided are processes for the tandem dehydrogenation of an alkane and dimerization of the produced alkene using an iridium pincer complex. The reaction is in the gas phase and the solid iridium pincer complex is heterogenized on magnesium silicates solid support (for example, $MgO \cdot \chi SiO_2$ such as Florisil®). The process allows an efficient upgrade of low molecular alkanes to fuel grade medium weight ($C_7+$) hydrocarbons.

The present process for producing dimerized alkenes comprises providing an iridium pincer complex bound to a solid support comprising magnesium silicates; providing a gaseous alkane feedstock comprising at least one alkane; and contacting the gaseous alkane feedstock with the iridium pincer complex bound to the solid support in the presence of a hydrogen acceptor to form dimerized alkenes. In one embodiment the support is magnesium silicates (for example, $MgO \cdot \chi SiO_2$ such as Florisil®) and the dimerized alkene products in the $C_7+$ range are recovered. In one embodiment the process further comprises recovering the dimerized alkenes.

In the dehydrogenation reactions, hydrogen that is co-formed during the process is removed for the chemical reaction to proceed and to prevent the excess hydrogen from poisoning the catalyst. The hydrogen is removed by using an olefin hydrogen acceptor, for example, ethylene or propene.

The present processes are conducted at lower reaction temperatures and exhibit unprecedented high turnover numbers (TONs). The present processes can show as high as 700 TON or greater at 10 minutes (based on iridium catalyst) and a turnover frequency (TOF) of 4250 TOh$^{-1}$ or greater for olefin production. More importantly, it has been surprisingly found that the present process offers a TON of at least 100 at 10 minutes for $C_7+$ products, and at least 185 at 40 minutes. For $C_7$ products, the TON at 10 minutes can be at least 35, and for dimerized $C_8$ products the TON at 10 minutes can be at least 65, with the formation of each being at a rate of 210 and 390 TOh$^{-1}$ respectively. After 40 minutes, the TON for $C_8$ dimer products can be at least 125.

It has also been found that the present process shows good recyclability of the catalyst, which is a great economic benefit. The catalyst remains active for up to four cycles. In the fourth cycle, the present processes can have a TON of at least 40 at 10 minutes The dehydrogenation reaction is conducted in a closed system and the hydrogen produced reacts with a hydrogen acceptor molecule. The hydrogen acceptors can be ethylene, propene, benzene, and the like, or mixtures thereof. In certain hydrogen acceptor embodiments, the hydrogen acceptors utilized are selected from the group consisting of ethylene, propene, and mixtures thereof. Ethylene, propene, and mixtures thereof are highly abundant light alkenes, readily recyclable, and inexpensive. Propene and ethylene are obtained in abundance as a by-product of oil refining and natural gas processing.

As such, provided are processes utilizing a hydrogen acceptor selected from the group consisting of ethylene, propene, and mixtures thereof. These hydrogen acceptors can be coordinated with the metal center of the iridium pincer complex. The processes using a hydrogen acceptor comprise utilizing ethylene or propene with an iridium pincer complex on a solid support to dehydrogenate an alkane feedstock, and then surprisingly dimerize the alkene product at a reasonable rate. The combination of the dehydrogenation and dimerization provides the tandem nature of the disclosed process.

The alkanes to be dehydrogenated can be $C_1$-$C_5$ alkanes, which are then upgraded in the present tandem dehydrogenation/dimerization process. The use of iridium pincer complex catalysts disclosed herein has been found to give unprecedented TONs for alkane dehydrogenation and dimerization in the gas phase when the catalyst is bound to magnesium silicates (for example, $MgO \cdot \chi SiO_2$ such as Florisil®) as a support. In some embodiments neutral alumina has also been found to be a good support for the iridium pincer catalyst. The present processes can show a rate of 700 TON or greater at 10 minutes (based on iridium catalyst) and a turnover frequency (TOF) of 4200 TOh$^{-1}$ or greater.

Among other factors, it has been discovered that the transfer dehydrogenation of alkanes, such as highly abundant light alkanes like butane and pentane, can be accomplished in the gas phase using readily recyclable and cheap hydrogen acceptors with unprecedented turnover numbers (TONs) and conversion rates. The hydrogen acceptors are alkenes such as propene and ethylene. It has also been discovered that, by reaction in the gas phase with the iridium pincer catalyst heterogenized on magnesium silicates (for example, $MgO \cdot \chi SiO_2$ such as Florisil®) unprecedented tandem dimerization of the alkenes formed occur. The dimerization reaction also occurs with unprecedented TON and turnover rate. This allows for $C_7+$ valuable fuel grade hydrocarbons to be recovered. In some embodiments the dimerized alkenes are $C_{7-19}$.

As used herein, the term "TON" (turnover number) refers to the alkenes produced by a mole of iridium pincer complex before it is inactivated or, alternatively, the hydrogen acceptor consumed by a mole of iridium pincer complex before it is inactivated. Increased TONs are associated with increased conversion. For example, the present processes can show a rate of 700 TON or greater at 10 minutes (based on iridium catalyst) and a turnover frequency (TOF) of 4000 TOh$^{-1}$ (turnovers per hour) or greater. The term "TOh$^{-1}$" (turnovers per hour) means how many feed molecules each catalyst molecule converts per hour. This is a measure of catalytic reaction rate, normalized to the amount of catalyst. For the dimerized products, a TON of at least 100 at 10 minutes and at least 185 at 40 minutes can be realized. For $C_7$ products, the TON at 10 minutes can be at least 35 and for $C_8$ products at least 65, with the formation rate of each being 210 and 390 $TOh^{-1}$ respectively.

Iridium Pincer Complex

As used herein, the term "iridium pincer complex" refers to a complex having a tridentate ligand that is connected to iridium via at least one metal-carbon sigma bond with substituents ortho to this sigma bond being held in a fixed position and coordinating to iridium.

In certain embodiment, the iridium pincer complex can have the following Formula I:

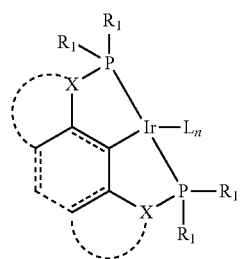

wherein the unspecified optionally fused ring system can be any C—H construction including optional O and N heteroatoms, including non-fused systems and fused ring systems such as naphthalenes; "n" is an integer from 0 to 4 and each L is independently H, alkyl, or alkene;

each $R_1$ is independently alkyl; and each X is independently O or $CH_n$, where n=0, 1 or 2.

In certain embodiments, the iridium pincer complex can have the following Formula (Ia):

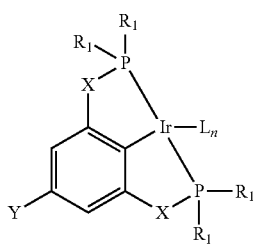

wherein:

"n" is an integer from 0 to 4 and each L is independently H, alkyl, or alkene;

each $R_1$ is independently alkyl;

each X is independently O or $CH_2$; and

Y is H or OM wherein M is alkyl, potassium (K), or solid support. When M is a solid support, the iridium pincer complex is bound to the solid support through a functional group.

In certain embodiments, the iridium pincer complex can have the following Formula (Ib):

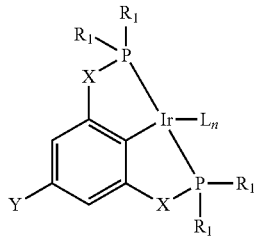

wherein:

"n" is an integer from 0 to 4 and each L is independently H or alkyl;

each $R_1$ is independently alkyl;

each X is independently O or $CH_2$; and

Y is H or OM wherein M is alkyl, K, or solid support.

In certain embodiments, the iridium pincer complex can have the following Formula

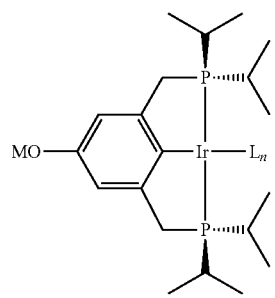

wherein M is potassium (K) or solid support; "n" is an integer from 0 to 4; and each L is independently H, alkyl, or alkene.

In certain embodiments, the iridium pincer complex can be (p-OM-$^{iPr4}$PCP)Ir($C_2H_4$) or (p-OM-$^{iPr4}$PCP)Ir($C_3H_6$), wherein M is K or a solid support. When M is a solid support, the iridium pincer complex is bound to the solid support through a functional group.

As used herein, in connection with the above Formulae, the term "alkyl" means a branched or straight chain, saturated hydrocarbon radical having 1 to 10 carbons. Exemplary alkyl groups include methyl, ethyl, n-propyl, isopropyl, n-butyl, sec-butyl, isobutyl, tert-butyl, and the like. In certain embodiments, the alkyl has 1 to 5 carbons. In other embodiments, the alkyl has 1 to 4 carbons.

As used herein, in connection with the above Formulae for the iridium pincer complex, the term "alkene" means a branched or straight chain, unsaturated hydrocarbon having 2 to 5 carbons and one carbon-carbon double bond. Exemplary alkene groups include ethylene, propene, but-1-ene, but-2-ene, and 2-methylpropene. In certain embodiments, the alkene has 2 or 3 carbons. In these embodiments, the alkene is ethylene or propene.

The iridium pincer complex can be as described in U.S. Pat. No. 6,982,305 to Nagy, which is incorporated herein by reference in its entirety.

In certain embodiments the iridium pincer complex can also be selected from the group consisting of:

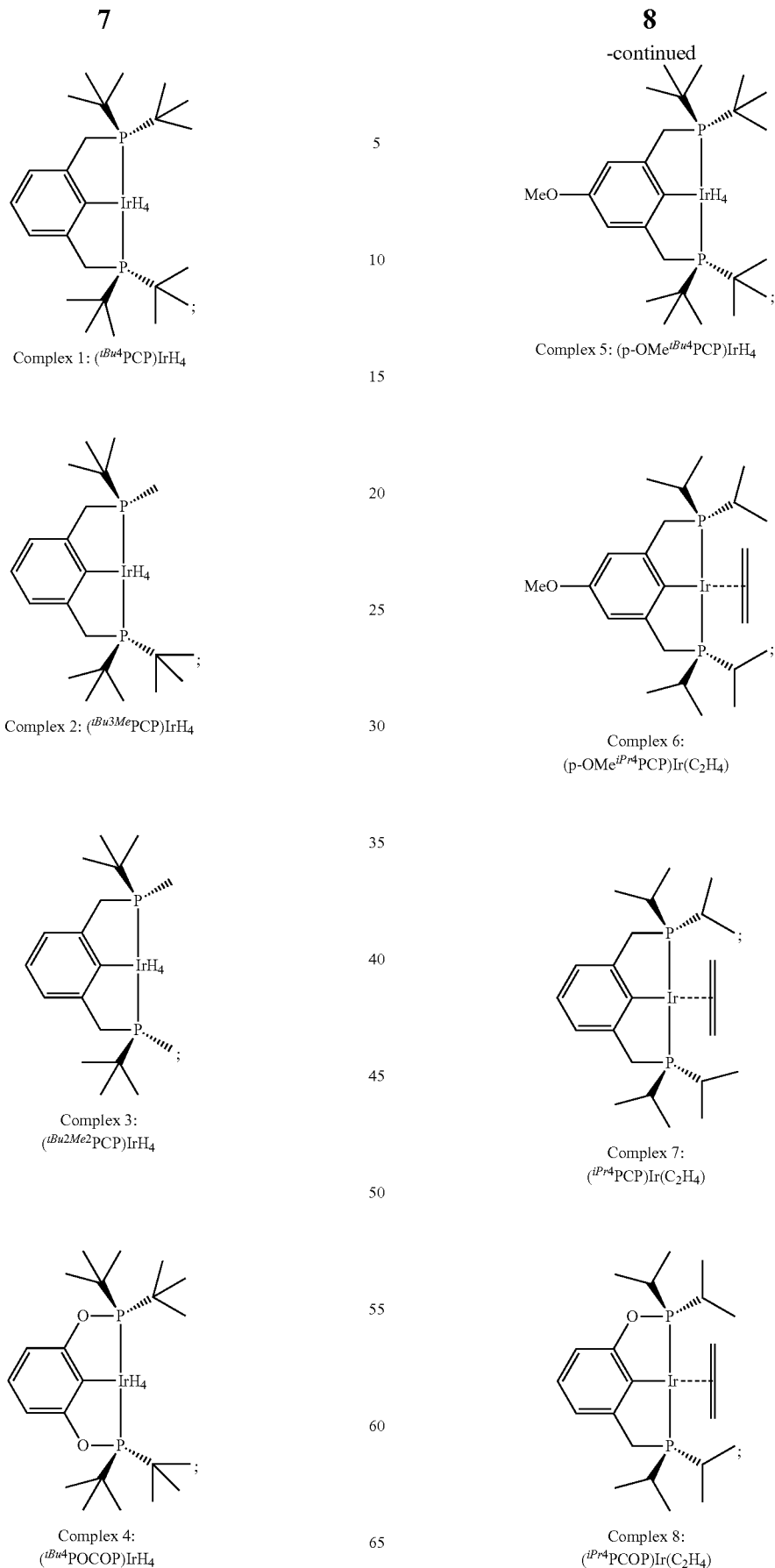

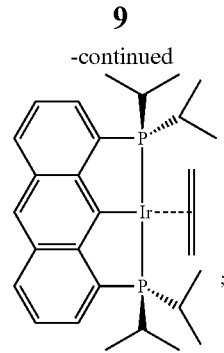

Complex 9:
($^{iPr4}$Anthraphos)Ir(C$_2$H$_4$)

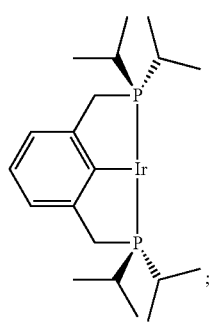

Complex 10: ($^{iPr4}$PCP)Ir

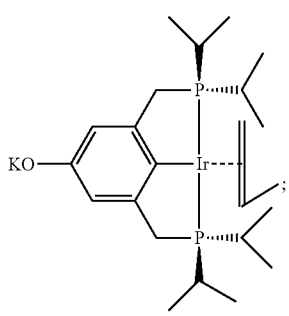

Complex 11:
(p-OK-$^{iPr4}$PCP)Ir(C$_3$H$_6$)

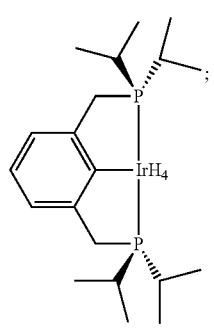

Complex 12:
($^{iPr4}$PCP)IrH$_4$

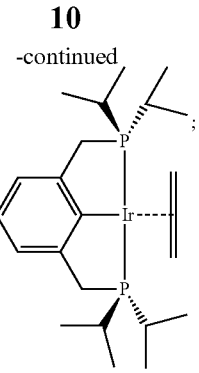

Complex 13:
(p-OK-$^{iPr4}$PCP)Ir(C$_2$H$_4$)

and mixtures thereof.

The iridium pincer complexes are immobilized on a solid support. When supported on a solid support, the iridium pincer complex is anchored via a covalent bond. The iridium pincer complexes, for the purposes of the present application, are heterogenized on magnesium silicates (for example, MgO.χSiO$_2$ such as Florisil®). It is noted that Florisil® is available from Sigma-Aldrich. In other embodiments, the solid support can be, for example, neutral alumina. In one embodiment, the pincer complexes have an anchoring group such as —OMe (i.e., —OCH$_3$) or —OK, which help bond the catalyst to the support.

In one embodiment of the present processes, the iridium pincer complex utilized is Complex 13 (p-OK-$^{iPr4}$PCP)Ir (C$_2$H$_4$). Complex 13 is immobilized on a solid support. The solid support can be magnesium silicates (for example, MgO.χSiO$_2$ such as Florisil®) or neutral alumina. In one embodiment for purposes of preparing and recovering dimers, Complex 13 (p-OK-$^{iPr4}$PCP)Ir(C$_2$H$_4$) is immobilized on magnesium silicates (for example, MgO.χSiO$_2$ such as Florisil®).

When the iridium pincer complex is immobilized on a solid support and used in a gaseous reaction, it can exhibit unexpected advantages in the tandem dehydrogenation dimerization process disclosed herein. In one embodiment, the iridium pincer complex immobilized on a solid support can dehydrogenate an alkane to produce an alkene and dimerize the alkene in the presence of a hydrogen acceptor such as ethylene or propene with unprecedented conversion rates and TONs. The supported iridium pincer complex can also exhibit better activity and recyclability in the process disclosed herein than an unsupported complex.

It has been discovered that the iridium pincer complex of the present processes immobilized on a solid support of magnesium silicates (for example, MgO.χSiO$_2$ such as Florisil®) can catalyze the tandem reactions of dehydrogenation and alkane dimerization at lower temperatures (160° C.-260° C.) with unprecedented TONs and conversion rates.

Alkane Feedstock

The alkane feedstock is gaseous and comprises at least one alkane. As used herein, the term "alkane" refers to a branched or straight chain, saturated hydrocarbon having from 1-5 carbons, more preferably from 4-5 carbons. Exemplary alkanes include n-butane, isobutane, n-pentane, isopentane, and neopentane. The alkane can be, for example, a butane (e.g. all isomers of butane, including, for example, n-butane, 2-methylpropane, and the like), or a pentane (e.g. all isomers of pentane, including, for example, n-pentane, 2-methylbutane, and the like). In an embodiment, the alkane comprises a butane. In another embodiment, the alkane comprises a pentane. In certain embodiments, the alkane is a straight chain alkane.

The alkane feedstock can comprise a single alkane or a mixture of alkanes. As such, the alkane to be dehydrogenated can be a single alkane or a mixture of alkanes. The alkane can be a mixture of isomers of an alkane of a single carbon number. The alkane feedstock can comprise hydrocarbons in addition to the alkane or mixture of alkanes to be dehydrogenated. A hydrocarbon feed composition from any suitable source can be used as the alkane feedstock.

Alternatively, the alkane feedstock can be isolated from a hydrocarbon feed composition in accordance with known techniques such as fractional distillation, cracking, reforming, dehydrogenation, etc. (including combinations thereof). For example, n-paraffin as a feed can be obtained by either by adsorption or extractive crystallization. One suitable source of the alkane feedstock described further herein, by no means to be taken as limiting, is the output of a Fischer-Tropsch reaction system.

The production of hydrocarbon compositions comprising alkanes from synthesis gas by Fischer-Tropsch catalysis is well known and can be carried out in accordance with known techniques by reaction of a synthesis gas in the presence of Fischer-Tropsch catalyst in a reactor. Any suitable catalyst can be used, including but not limited to iron and cobalt catalysts. See, e.g., U.S. Pat. No. 6,217,830 to Roberts and Kilpatrick; see also U.S. Pat. Nos. 6,880,635; 6,838,487; 6,201,030; 6,068,760; 5,821,270; 5,817,701; 5,811,363; 5,620,676; and 2,620,347.

The production of synthesis gas from carbonaceous or organic materials, such as coal (including coal fines), natural gas, methane, refinery bottoms, vegetative materials such as wood or other biomass, and combinations thereof, is well known and can be carried out in accordance with known techniques. In some embodiments such production involves the partial oxidation of the carbonaceous or organic material at elevated temperatures, and optionally elevated pressures, with a limited volume of oxygen. The reaction is preferably carried out in a reactor into which the material is fed, together with additional agents such as steam, carbon dioxide, or various other materials. See e.g., U.S. Pat. No. 4,959,080; see also U.S. Pat. No. 4,805,561.

Dimerized Alkene Product

The gaseous alkane feedstock is dehydrogenated to form an alkene product. The alkene product is then dimerized to form dimerized alkenes. The alkene product comprises at least one alkene. As used herein, in connection with the alkene product, the term "alkene" refers to a branched or straight chain, unsaturated hydrocarbon having 4 to 8 carbons and one or more carbon-carbon double bonds. The alkene product is dimerized to form dimerized alkenes. The reaction is a tandem reaction and as such, the dehydrogenation is directly followed by dimerization without isolation of an intermediate product. In one embodiment the dimerized alkene product are $C_{7+}$ and in certain embodiments are $C_{7-19}$.

The alkene product can contain an alkene with one double bond, a diene (i.e., an alkene with two carbon-carbon double bonds), a dimer, and mixtures thereof. The present process provides the dimers in unprecedented conversion rates and TON.

Reaction Conditions

In general, the dehydrogenation/dimerization reaction can be run under conventional dehydrogenation reaction conditions. However, the iridium pincer complexes disclosed herein do not require high temperatures or pressures. Therefore, the reaction can be run at a reaction temperature less than 300° C. Higher temperatures up to 400° C. or 500° C. or higher can be used, but are not necessary and are not desired. Suitable temperatures include, for example, a temperature in the range of 160° C.-260° C. In certain embodiments a temperature in the range of 200° C.-260° C. can be utilized. In other embodiments, a temperature in the range of 225° C.-250° C. can be utilized. In yet other embodiments a temperature in the range of 240° C.-250° C. can be utilized. In an embodiment, a temperature of about 240° C. is used, which temperature is sufficient to maintain ethylene or propylene in the gaseous phase. In another embodiment, a temperature of about 200° C. is used. In yet another embodiment, a temperature of about 160° C. is used. The pressure is adjusted accordingly.

Conducting the dehydrogenation reaction at temperatures of less than 300° C. (e.g., 160° C.-260° C.) results in extremely little to no cracking of the alkane feedstock. Accordingly, the present dehydrogenation reactions can be run with unprecedented selectivities.

The length of reaction time with best results for selectivity varies based upon the catalyst. The reaction time is generally in the range of from about 1 minute or less (e.g., about 30 seconds) up to 24 hours. The reaction time can be up to about 10 minutes, up to about 40 minutes, up to about 80 minutes, up to about 100 minutes, up to about 180 minutes, or up to about 600 minutes. The reaction time can be about 10 minutes, about 40 minutes, about 80 minutes, about 100 minutes, about 180 minutes, or about 600 minutes. In one embodiment, the reaction time is from about 10-100 minutes. Alternatively, the reaction time can be from about 10-180 minutes. In another embodiment, the reaction time can be from about 20-180 minutes. In another embodiment, the reaction time can be from about 40-100 minutes. In yet another embodiment, the reaction time can be from about 40-180 minutes. The reaction time can be from about 10-40 minutes, about 10-80 minutes, about 10-100 minutes, about 10-180 minutes, or about 10-600 minutes.

The reaction takes place in the presence of a solid catalyst and a gaseous hydrogen acceptor and a gaseous alkane. The use of a solid catalyst has been found to work well with a gaseous phase for the alkane and for the hydrogen acceptor. In particular, the use of a solid iridium pincer catalyst heterogenized on magnesium silicates (for example, $MgO \cdot \chi SiO_2$ such as Florisil®) has been found to work surprisingly well in the processes as disclosed herein.

As used herein, the term "gas phase" refers to the alkane and the hydrogen acceptor both being gaseous during the dehydrogenation reaction. However, during the "gas phase" reaction, the catalyst is solid. In an embodiment, the reaction is conducted under supercritical conditions.

The following examples are provided to better illustrate the process disclosed herein. The examples are meant to be solely illustrative, and not limiting.

EXAMPLE 1

In a typical supported heterogeneous gas-phase dehydrogenation experimental set-up, the catalyst (p-OK-$^{iPr4}$PCP)Ir($C_2H_4$) in sealable ampoule was solubilized in a 100 µl solvent to give a 1 mM solution and 10 mg of the solid support was added to solution with stirring. The color of the solution gradually disappears and the solid support acquires this color indicating heterogenization of the catalyst. Solvent was then removed under vacuum to yield a free flow supported catalyst. The vials were then sealed under 6 atm of a butane/propene (1:1) gas mixture. One should note that contrary to unsupported heterogeneous systems, coating of the catalyst on walls is not feasible in these supported heterogeneous systems. Hence to attain better activity, the ampoules containing pentane and the supported catalysts were spun in an oven at 200° C. for a stipulated time. The vials were then cooled and the contents analyzed.

TABLE 1

(p-OK-$^{iPr4}$PCP)Ir($C_2H_4$) catalyzed gas phase dehydrogenation of n-butane [6.1] with propene [6.1M] as acceptor at 200° C. on various solid supports.

| Solid Support | Time | Total Olefin TON | Butadiene TON | 1-Butene TON | $C_7$ TON | $C_8$ TON |
|---|---|---|---|---|---|---|
| 2 mg Florisil/ MgO•χSiO$_2$ | 10 | 710 | 150 | 80 | 35 | 65 |
|  | 40 | 1130 | 250 | 100 | 60 | 125 |
| 2 mg Neutral Al$_2$O$_3$ | 10 | 130 | 30 | 10 | 5 | 10 |
|  | 40 | 315 | 45 | 20 | 15 | 15 |
| 2 mg Silica SiO$_2$ | 10 | 75 | 15 | 15 | 2 | 2 |
|  | 40 | 310 | 60 | 40 | 18 | 35 |

Table 1 summarizes the (p-OK-$^{iPr4}$PCP)Ir catalyzed gas phase dehydrogenation of n-butane [6.1] with propene [6.1 M] as acceptor at 200° C. on various solid supports. Florisil was found to give the best results with the dehydrogenation occurring at a rate of 4250 TOh$^{-1}$. Catalytic systems in which the (p-OK-$^{iPr4}$PCP)Ir was supported on neutral alumina and silica proceeded much more slowly and resulted in 780 and 450 TOh$^{-1}$ respectively. More interestingly in addition to the dehydrogenation products GC analysis revealed higher $C_7$ and $C_8$ fragments resulting from olefin dimerization. Particularly on using (p-OK-$^{iPr4}$PCP)Ir supported on Florisil, $C_7$ and $C_8$ dimerized alkene fragments are formed at a rate of 210 and 390 TOh$^{-1}$.

EXAMPLE 2

Catalyst recyclability studies were performed using the catalytic system based on (p-OK-$^{iPr4}$PCP)Ir supported on Florisil® (Table 2). These studies reveal that the catalyst is highly recyclable, i.e., can be used for numerous cycles, and proceeded at rates of 4260, 960, 300, and 240 TOh$^{-1}$ in the first, second, third and fourth cycle respectively.

TABLE 2

Recylability studies of (p-OK-$^{iPr4}$PCP)Ir/Florisil catalyzed gas phase dehydrogenation of n-butane [6.1] with propene [6.1M] as acceptor at 200° C. after 10 minutes

| Solid Support | Cycle | Total Olefin TON | Butadiene TON | 1-Butene TON | $C_7$ TON | $C_8$ TON |
|---|---|---|---|---|---|---|
| 2 mg Florisil MgO•χSiO$_2$ | First | 705 | 160 | 105 | 25 | 40 |
|  | Second | 160 | 35 | 20 | 5 | 10 |
|  | Third | 50 | 5 | 10 | 2 | 5 |
|  | Fourth | 40 | 5 | 5 | 5 | 5 |

The current invention therefore, provides an efficient alternative to upgrade unproductive and highly abundant low molecular weight alkanes to fuel grade medium weight hydrocarbons by a tandem alkane-dehydrogenation/alkene-dimerization reaction in the gas phase that is catalyzed by pincer ligated iridium catalysts heterogenized on solid supports such as magnesium silicates (for example, MgO.χSiO$_2$ such as Florisil®). The catalyst also shows good recyclability.

Various modifications and alterations of the process disclosed herein will become apparent to those skilled in the art without departing from the scope and spirit of the process disclosed herein. Other objects and advantages will become apparent to those skilled in the art from a review of the preceding description.

A number of patent documents and non-patent documents are cited in the foregoing specification in order to describe the state of the art to which the process disclosed herein pertains. The entire disclosure of each of the cited documents is incorporated by reference herein.

Furthermore, the transitional terms "comprising", "consisting essentially of" and "consisting of", when used in the appended claims, in original and amended form, serve to indicate what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed process. All iridium pincer complex catalysts and methods of use thereof embodied herein can, in alternate embodiments, be more specifically defined by any of the transitional terms "comprising", "consisting essentially of" and "consisting of".

That which is claimed is:

1. A process for preparing dimerized alkenes in a tandem dehydrogenation/alkene dimerization reaction comprising:
    providing an iridium pincer complex bound to a solid support comprising magnesium silicates;
    providing a gaseous alkane feedstock comprising at least one alkane;
    contacting the gaseous alkane feedstock with the iridium pincer complex bound to the solid support in the presence of a hydrogen acceptor to form the dimerized alkenes; and
    recovering the dimerized alkenes as recovered dimerized alkenes.

2. The process of claim 1, wherein the at least one alkane of the gaseous alkane feedstock comprises 4 or 5 carbons.

3. The process of claim 1, wherein the recovered dimerized alkenes comprise $C_{7+}$ dimerized alkenes.

4. The process of claim 3, wherein the recovered dimerized alkenes comprise $C_{7-19}$ dimerized alkenes.

5. The process of claim 1, wherein the hydrogen acceptor comprises ethylene, propene or mixtures thereof.

6. The process of claim 1, wherein the iridium pincer complex is (p-OM$^{iPr4}$PCP)Ir($C_2H_4$) bound to the solid support comprising magnesium silicate, where M is K or the solid support.

7. The process of claim 1, wherein the process has a TON for $C_{7+}$ products of at least 100 at 10 minutes.

8. The process of claim 1, wherein the process has a TON for $C_{7+}$ products of at least 185 at 40 minutes.

9. The process of claim 1, wherein the process is run for four cycles with a same iridium pincer complex bound to the solid support.

10. The process of claim 9, wherein the process has a TON for olefins in a fourth cycle of at least 40 at 10 minutes.

11. The process of claim 9, wherein the process has turnover frequency rates (TOF) of at least 4260, 960, 300, and 240 TOh$^{-1}$ in a first, a second, a third, and the fourth cycle respectively.

12. The process of claim 1, wherein the process has a TON for $C_8$ of at least 65 after 10 minutes and of at least 125 after 40 minutes.

13. The process of claim 1, wherein the iridium pincer complex has a Formula

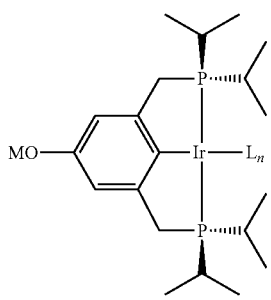

wherein M is K or the solid support; "n" is an integer from 0 to 4; and each L is independently H, alkyl, or alkene.

14. The process of claim 13, wherein L is ethylene.

15. The process of claim 1, wherein the iridium pincer complex is selected from the group consisting of:

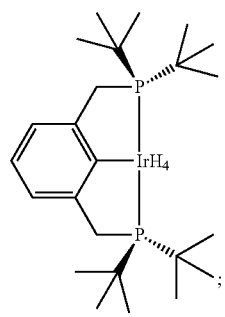

Complex 1: ($^{tBu4}$PCP)IrH$_4$

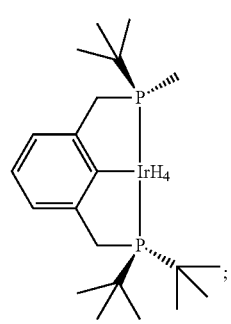

Complex 2: ($^{tBu3Me}$PCP)IrH$_4$

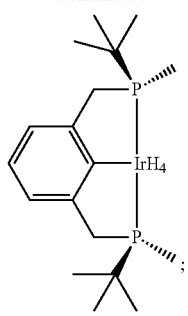

Complex 3: ($^{tBu2Me2}$PCP)IrH$_4$

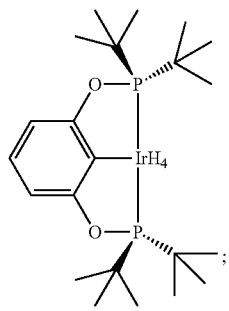

Complex 4: ($^{tBu4}$POCOP)IrH$_4$

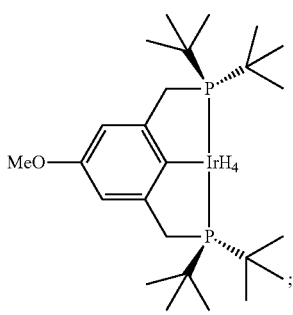

Complex 5: (p-OMe$^{tBu4}$PCP)IrH$_4$

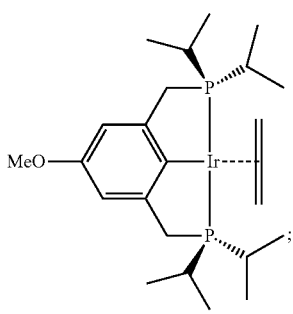

Complex 6: (p-OMe$^{iPr4}$PCP)Ir(C$_2$H$_4$)

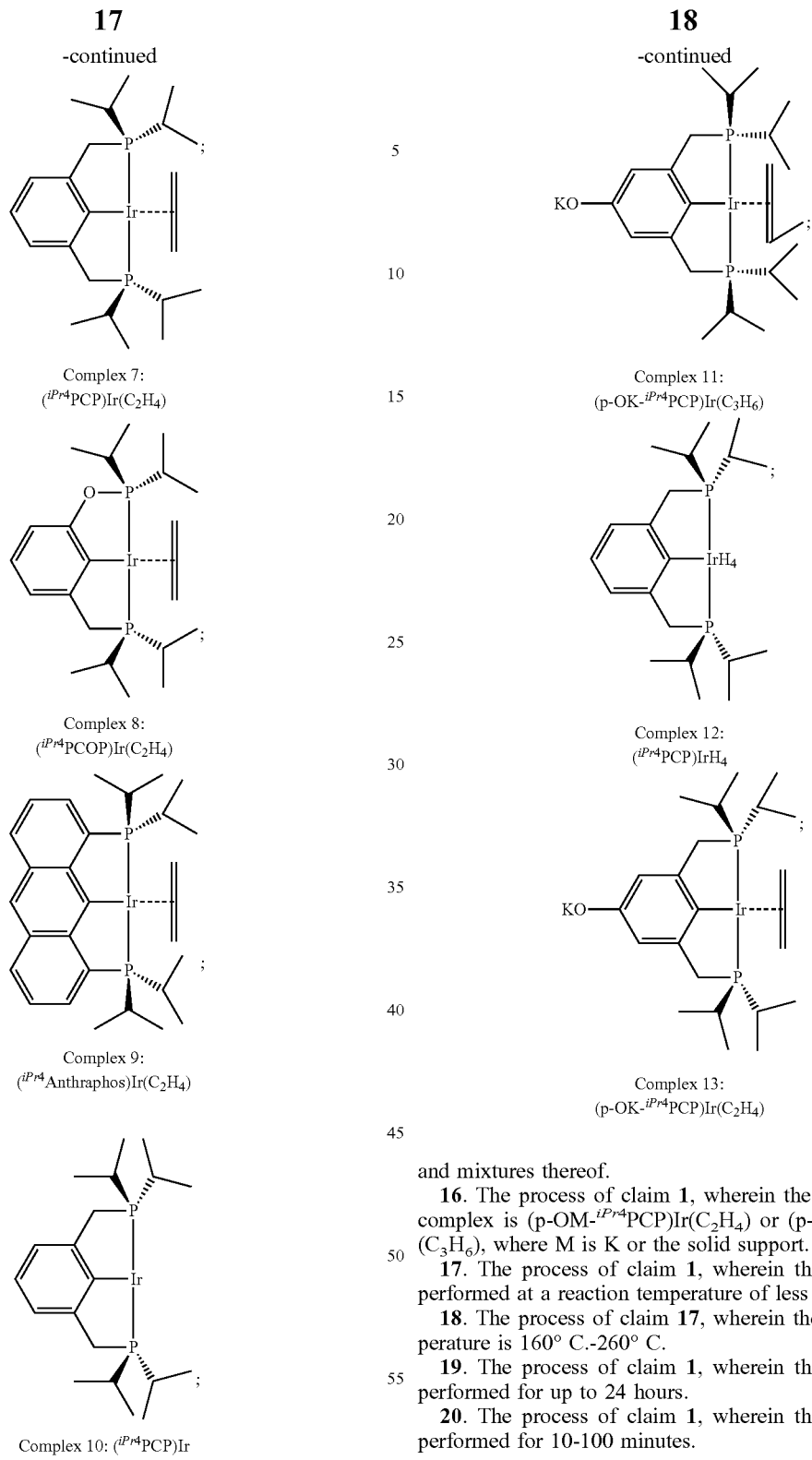

and mixtures thereof.

16. The process of claim 1, wherein the iridium pincer complex is (p-OM-$^{iPr4}$PCP)Ir(C$_2$H$_4$) or (p-OM-$^{iPr4}$PCP)Ir(C$_3$H$_6$), where M is K or the solid support.

17. The process of claim 1, wherein the contacting is performed at a reaction temperature of less than 300° C.

18. The process of claim 17, wherein the reaction temperature is 160° C.-260° C.

19. The process of claim 1, wherein the contacting is performed for up to 24 hours.

20. The process of claim 1, wherein the contacting is performed for 10-100 minutes.

* * * * *